United States Patent [19]

Evert

[11] 4,316,271
[45] Feb. 16, 1982

[54] PURGING AND EXPANSION MECHANISM

[75] Inventor: Donald A. Evert, Littleton, Colo.

[73] Assignee: Honeywell Inc., Minneapolis, Minn.

[21] Appl. No.: 224,897

[22] Filed: Jan. 14, 1981

[51] Int. Cl.³ .............................................. H04R 1/02
[52] U.S. Cl. ..................................... 367/140; 73/644;
   367/104; 367/171; 367/172; 181/402; 128/660
[58] Field of Search ................. 73/618, 619, 629, 633,
   73/634, 641, 644; 367/87, 166, 99, 167, 104,
   171, 120, 172, 140, 188; 181/402, 198, 139, 140,
   142; 128/660

[56] References Cited
U.S. PATENT DOCUMENTS 1,463,507  7/1923  Hahnemann .................... 181/402 X
4,215,585  8/1980  Kunii et al. ............................ 73/633

Primary Examiner—Richard A. Farley
Attorney, Agent, or Firm—Lockwood D. Burton;
Mitchell J. Halista

[57] ABSTRACT

A housing for an electroacoustic transducer includes a filling or access port for introducing an inert liquid into the chamber defined by the housing. The access port includes a bubble trap and a vent for extracting gaseous bubbles from the fluid fill. The structure of the access port also comprises a substantially zero spring pressure expansion cavity for the fluid.

6 Claims, 2 Drawing Figures

U.S. Patent  Feb. 16, 1982  4,316,271
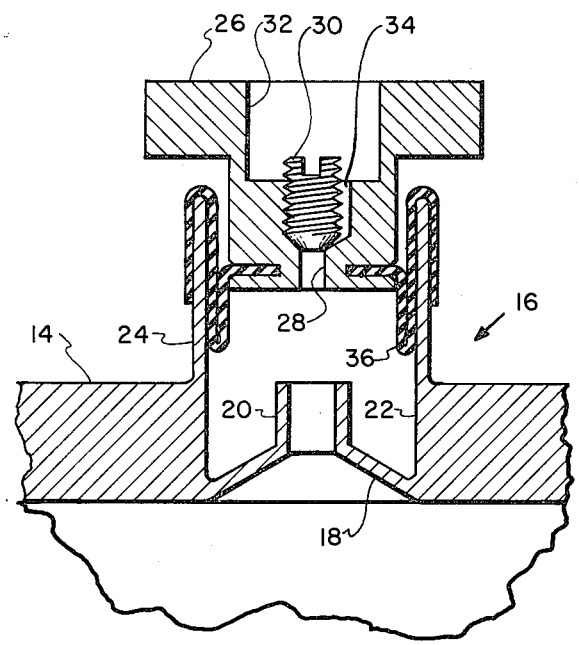
F I G. 2
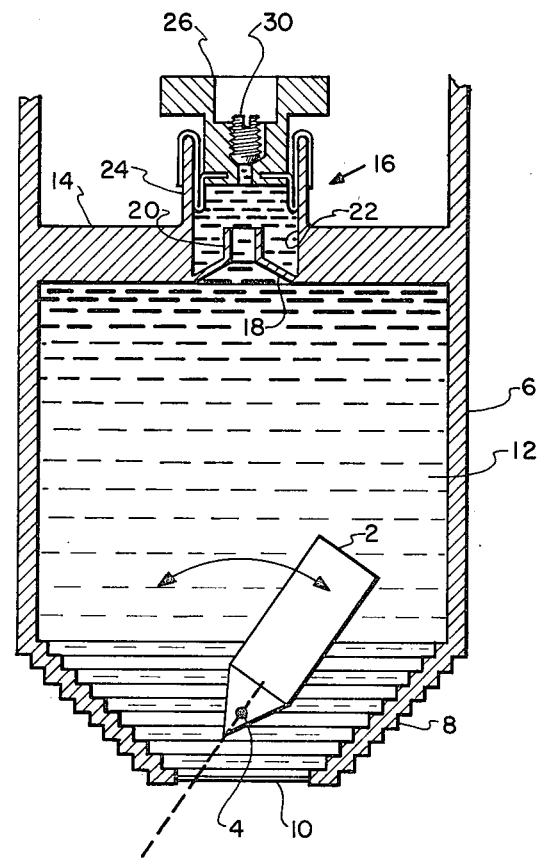
F I G. 1

PURGING AND EXPANSION MECHANISM

CROSS REFERENCES

Cross reference is made to a copending application of Dale O. Ballinger tilted Acoustic Transducer Housing bearing Ser. No. 173,859, filed July 30, 1980.

BACKGROUND OF THE INVENTION

The present invention relates to medical instrumentation apparatus. More particularly, it relates to improved housing means for an acoustic transducer.

In the art of medical diagnostics, one form of noninevasive examination of the internal organs of a body under examination involves the use of ultrasonic transducers. These transducers are frequently mounted within a housing filled with an inert liquid and arranged to oscillate in an angularly scanning motion. The housing is generally relatively opaque to the ultrasonic pulses generated by the transducer, with the exception of a relatively transparent window or diaphragm in the operating end of the housing structure. The transducer is positioned and oscillated to direct the acoustic pulses through the diaphragm or window, into the body under examination. The acoustic pulses transmitted into that body are then reflected back toward the transducer at interfaces of tissue within the body, to produce electrical pulses which may be translated into an image of the interior of the body being examined. As noted, the housing for the transducer is filled with an inert liquid. If there are air bubbles remaining within the housing, these air bubbles will be agitated into the liquid by the oscillation of the transducer. The entrained air bubbles cause a deterioration of the transmitted and received signals, thereby interfering with an accurate imaging of the organ under examination.

SUMMARY OF THE INVENTION

It is, accordingly, an object of the present invention to provide an improved transducer housing which obviates the foregoing shortcomings.

It is another object of the present invention to provide an improved transducer housing which includes means for purging air bubbles from the interior of the housing.

It is another object of the present invention to provide an improved transducer housing as set forth which features a zero spring rate expansion capacity for the chamber.

In accomplishing these and other objects, there has been provided, in accordance with the present invention, a housing for an acoustic transducer which includes a filling port for introducing the inert liquid into the chamber. The filling port includes a bubble trap for extracting gaseous bubbles from the fluid filled chamber.

BRIEF DESCRIPTION OF THE DRAWINGS

A better understanding of the present invention may be had from the following detailed description when read in the light of the accompanying drawings in which:

FIG. 1 is a cross sectional view of an acoustic transducer housing embodying the present invention; and FIG. 2 is an enlarged cross sectional view of the fill port bubble trap embodying the present invention.

DETAILED DESCRIPTION

In FIG. 1, there is shown a transducer 2 mounted for pivotal motion about an axis of rotation 4. The mechanism for causing the oscillatory motion of the transducer 2 is not illustrated in the present application, not being a part of the present invention. The transducer, however, and its driving mechanism is mounted within a housing member 6. The housing member 6 is generally cylindrical in shape but is provided with a substantially conical operating end 8, here illustrated as having an annularly stepped configuration. The body of the housing member 6 with its conical operating end 8 is substantially non-transparent to acoustic energy. The substantially conical operating end 8 is, however, truncated with the truncated portion provided with an acoustically transparent window 10. The interior of the housing member 6 is filled with an appropriate fluid 12. In a manner well known in the art, the fluid 12 is of the type which provides the necessary acoustic coupling between the transducer 2 and the window 10 and yet has such electrical properties as would not interefere with the electrical operation of the transducer.

It is highly desirable that the fluid 12 completely fill the interior of the housing member 6 in which the transducer is mounted. Any residual air or other gases trapped in the compartment would, under agitation by the motion of the transducer, produce a number of bubbles which would be mixed with the coupling fluid 12. These bubbles would produce a mechanical interface for the acoustic energy transmitted or received by the transducer 2. Such mechanical interfaces would produce, in turn, highly undesirable noise signals which would then tend to obfuscate the desired image. The structure in accordance with the present invention provides means for allowing the interior chamber defined by the housing member 6 to be completely filled with the fluid, initially. Then, such gases as may be evolved within the chamber through use may be removed from the chamber and replaced with additional fluid, under field conditions.

To the accomplishment of that end, the housing member 6 is provided with a relatively thick back wall 14. Located in that back wall there is provided an access port 16 for the admittance of the fluid 12 and for the expulsion of entrapped gases from the compartment or chamber. The access port is constructed to include an inverted funnel shaped central element 18 with the larger or outer rim of the funnel being coextensive with the inner wall surface of the back wall 14. The inner or smaller dimension of the tapered surface of the funnel element 18 terminates in an upwardly extending cylindrical spout or neck 20. A substantially cylindrical cavity 22 is formed through the back wall 14 and has its lower extremity sealed to or unitary with the perimeter of the funnel portion 18. A relatively thin walled cylindrical portion 24 extends the cavity 22 above the upper surface of the back wall 14. A plunger 26 is positioned to be moved into and out of the cavity defined by the cylindrical extension 24.

As may be more clearly seen in FIG. 2, the plunger is provided with a central bore 28, a first counterbore into which a set screw 30 is threaded, and a larger counterbore 32. A bleed hole 34 is provided contiguous with the first counterbore but does not extend to the full depth of the first counterbore. A flexible rolling diaphragm 36 couples the plunger 26 to the walls of the cylindrical extension 24. To this end, the outer end of the diaphragm member 36 overlies the outer surface of the upper end of the cylindrical extension 24 and is secured thereto as by a suitable cement. The diaphragm member 36 is then folded over the end of the cylindrical member 24 and extends loosely along the inner wall thereof to a point whereat the diaphragm is then folded back upon itself, with the inner end thereof secured in an annular groove in the lower end of the plunger 26. As the plunger is moved into and out of the cavity 22, the folded back portion of the diaphragm member 36 rolls on itself to maintain a sealed relationship between the interior of the cavity 22 and the exterior thereof and yet does not impose a significant spring force or pressure on the fluid as a result of the position of the plunger.

In initially filling the chamber within the housing member 6, the set screw 30 may be removed and the fill material introduced into the cavity through the central bore 28 and the cylindrical neck 20 of the inverted funnel structure 18. As the chamber becomes filled, the fluid will overflow the neck of the funnel 20 into the cavity 22, preferably with the plunger 26 withdrawn a significant distance. When the cavity 22 has been appreciably filled, the housing structure is allowed to rest in a vertical position. Under these conditions, any entrapped bubbles will work their way to the top of the fluid in the main housing chamber and through the funnel structure 18 into the cavity 22. In the meantime, the set screw 30 will have been replaced in the first counterbore of the plunger, but not completely seated. When sufficient time has elapsed for the entrained bubbles to have all accumulated in the cavity 22, the plunger may be pressed downward forcing the bubbles up through the inner bore 28 and the bleed hole 34 to escape into the atmosphere. An excess of fluid may be placed in the second counterbore which now comprises a reservoir for the excess fluid. The plunger 26 is depressed, gently, until no more bubbles issue from the bleed hole 34. The plunger may then be withdrawn slightly to draw a portion of the excess fluid through the bleed hole and into the cavity 22. The set screw 30 may then be tightened to seal the cavity at the bottom of the first counterbore.

If, after the apparatus has been in use for sometime, gases develop within the housing 6, small quantities of such gases may be accumulated in the cavity 22 by holding the apparatus in the vertical position illustrated in FIGS. 1 and 2, allowing the bubbles of gas to move toward the funnel structure 18 and into the cavity 22. The configuration of the funnel structure 18 with its neck 20 defines a trap for such gases such that when the housing member 6, with its associated transducer, is placed in some operating position other than the illustrated vertical position, the bubbles of gas will not return to the main chamber of the housing 6 but will remain trapped in the cavity 22. When a sufficient quantity of gas has been accumulated in the cavity 22 the gas may be removed from the cavity 22 by positioning the housing structure in the illustrated vertical position, pouring a quantity of the desired fluid in the reservoir 32, loosening the set screw 30 to open the passage 34. The plunger 26 may then be gently depressed to force the accumulated gases up through the bore 28 and the bleed hole 34 to the exterior of the structure where they may escape to the atmosphere. The plunger 26 may then be gently pulled backward causing the fluid, or a portion thereof, in the reservoir 32 to be drawn into the cavity 22 replacing the extracted gases. The set screw 30 may then again be tightened to seal the entire structure. Thus restored, even under field conditions, the transducer may be returned to operating conditions quickly.

The housing itself as well as the fluid contained therein may be subjected to thermal expansion and contraction. If the structure were completely fixed and sealed, there would be a corresponding change in the pressure within the contained fluid. This change in pressure may, indeed, produce a significant change in the response characteristic of the transducer 2. The rolling diaphragm 36, in addition to the movement of the plunger 26 during filling and purging operations of the structure, also provides a convenient expansion connection allowing the plunger 26 to be moved in response to changes in internal pressure of the fluid without imposing an undesirable spring loading affect upon the fluid within the chamber.

Thus, there has been provided, in accordance with the present invention, an improved housing structure for an acoustic transducer which structure provides improved means for purging air from a contained fluid and which provides means for thermal expansion of the fluid without imposing undesirable spring forces on the fluid.

The embodiments of the invention in which an exclusive property or privilege is claimed are as follows:

1. A housing structure for an electroacoustic transducer comprising:
   a main housing body portion defining a chamber in which the transducer is mounted;
   said body portion having a wall member;
   an access port in said wall member through which fluid fill may be admitted to said chamber and through which gases in said chamber may be purged;
   said access port including means defining a bubble trap cavity and a plunger means having a selectively opened bleed hole.

2. A housing structure as set forth in claim 1 wherein said means defining said bubble trap cavity includes a funnel shaped member at the chamber end of said cavity with the funnel extending into said cavity, whereby gaseous bubbles in said fluid fill pass through said funnel shaped member into said cavity.

3. A housing structure as set forth in claim 2 wherein said plunger means includes a central bore and a first counterbore therethrough, said first counterbore being tapped to receive a set screw, and a bleed hole extending contiguous with said first counterbore but less than the full depth thereof whereby said set screw may be selectively loosened to open said bleed hole and tightened to close said bleed hole.

4. A housing structure as set forth in claim 3 wherein said plunger means includes a second and larger counterbore at the outward end of said plunger means, said second counterbore comprising a reservoir for replacement fill fluid.

5. A housing structure as set forth in claim 4 wherein said plunger means is connected to the outer end of said means defining said cavity by a flexible sealing member.

6. A housing structure as set forth in claim 5 wherein said flexible sealing member comprises a rolling diaphragm.

* * * * *